United States Patent [19]

Braden et al.

[11] 3,989,743
[45] Nov. 2, 1976

[54] PROCESS FOR THE PREPARATION OF 4,4'-DIAMINOSTILBENE-2,2'-DISULPHONIC ACID

[75] Inventors: Rudolf Braden, Odenthal-Scheuren; Hans Knupfer, Schildgen, both of Germany

[73] Assignee: Bayer Aktiengesellschaft, Leverkusen, Germany

[22] Filed: Dec. 11, 1974

[21] Appl. No.: 531,751

[30] Foreign Application Priority Data

Dec. 18, 1973 Germany............................ 2362781

[52] U.S. Cl.................................. 260/510; 260/508
[51] Int. Cl.²........................................ C07C 143/56
[58] Field of Search..................... 260/510, 508, 580

[56] References Cited
UNITED STATES PATENTS

| | | | |
|---|---|---|---|
| 2,636,901 | 4/1953 | Tindall | 260/580 |
| 2,784,220 | 3/1957 | Spiegler | 260/580 |

*Primary Examiner*—James O. Thomas, Jr.
*Assistant Examiner*—Nicky Chan
*Attorney, Agent, or Firm*—Plumley and Tyner

[57] ABSTRACT

Process for the preparation of 4,4'-diaminostilbene-2,2'-disulphonic acid or its alkali salts by catalytic hydrogenation of 4,4'-dinitrostilbene-2,2'-disulphonic acid in an aqueous medium, characterized in that the hydrogenation is carried out on a cobalt catalyst at 70°–180° C and 5–150 bars of $H_2$, at a pH value between 6.0 and 8.5.

6 Claims, No Drawings

PROCESS FOR THE PREPARATION OF 4,4'-DIAMINOSTILBENE-2,2'-DISULPHONIC ACID

The subject of the invention is a technically simple process for the preparation of 4,4'-diaminostilbene-2,2'-disulphonic acid by catalytic reduction of 4,4'-dinitrostilbene-2,2'-disulphonic acid in the form of the water-soluble alkali metal salts.

4,4'-Diaminostilbene-2,2'-disulphonic acid is an important intermediate product for the preparation of optical brighteners.

The reduction of 4,4'-dinitrostilbene-2,2'-disulphonic acid — hereafter referred to as dinitro-acid — has hitherto been carried out with iron in acid solution. In this process, after the reduction, a considerable technical effort is required in order to separate the reducing agent from the 4,4'-diaminostilbene-2,2'-disulphonic acid — hereafter referred to as diamino-acid — the iron arising as an iron hydroxide sludge which is difficult to filter and which, in order that it can be dumped or utilised technically, must be worked up by drying or roasting.

The practically iron-free quality required for use as a starting product for optical brighteners can only be achieved with difficulty after the process of reduction with iron.

It has been found that diamino-acid can be prepared by catalytic hydrogenation of dinitro-acid. The process according to the invention is characterised in that an alkali metal salt of dinitro-acid is hydrogenated on a cobalt catalyst, or catalyst containing cobalt, in particular on Raney cobalt, in the temperature range of 70° to 180° C under a hydrogen pressure of 5 to 150 bars in an aqueous medium in the pH range of 6.0 to 8.5.

This process gives a diamino-acid in more than 95% yield and in high purity. This is all the more surprising since hitherto no generally industrially applicable process for the selective catalytic reduction of nitro groups next to double bonds was available.

The literature contains contradictory statements on the hydrogenation of 3-nitrostilbene (M. Freifelder: Practical Catalytic Hydrogenation, N.Y. 1971, page 193). Using nickel, 1,4-bis-(3-nitrostyryl)-benzene is attacked both at the nitro groups and at the double bonds.

Again, when using platinum catalysts, selective hydrogenation of the nitro group next to the olefinic double bond is only possible in special cases (Rylander: Catalytic Hydrogenation over platinum Metals, N.Y. 1967, page 178 and F. Zymalkowski: Katalytische Hydrierungen im organischchemischen Laboratorium (Catalytic Hydrogenations in Organic Chemistry Laboratories), Enke-Verlag, 1965).

The catalytic reduction of p-nitrophenyl acrylate on various catalysts gives p-nitrophenyl propionate. Dinitro-acid is reduced on nickel catalysts to diamino-acid with large proportions of 4,4'-diaminodibenzyl-2,2'-disulphonic acid.

The cobalt catalyst employed according to the invention can be employed in the reduced form or be obtained by reduction from cobalt compounds under the conditions of the process. It can be advantageous to add to the catalyst promoters such as metals of atomic numbers 21 to 79, in proportions of 3–0.001% relative to cobalt. The catalyst can also be used precipitated on a support.

The dinitro-acid is preferably employed in the form of its alkali metal salts, especially as the disodium salt, in aqueous solution or suspension.

According to the invention, the solution or the suspension is adjusted to pH 6–8.5, especially to pH 6.2–7.

In a preferred embodiment, a solution of the alkali metal salt of the dinitro-acid, which has a pH value above 7, is treated with carbon dioxide until a pH value of 6.5–7 has been obtained.

The process according to the invention can be carried out at a temperature of 70°–180° C, in particular 100°–160° C. In a preferred embodiment, temperatures of 120°–150° C are used. The hydrogen pressure can be 5–150 bars. In particular, 50–100 bars of $H_2$ are used.

The process can be carried out as a sump phase hydrogenation over a pulverulent cobalt contact catalyst or over a particulate cobalt contact catalyst which is optionally in a fixed position, and can be carried out batchwise or continuously, for example in a stirred kettle cascade or a tubular reactor. It can be advantageous to carry out the process continuously in trickle phase. The catalyst can be separated off in the usual manner, by filtration.

The solutions of the alkali metal salts of diaminostilbene-acid, obtained according to the process of the invention, are light yellow in color and can be employed without further purification processes for the preparation of optical brighteners. This is a further particular advantage of the process.

EXAMPLE 1

600 g of a water-moist paste of industrially manufactured disodium 4,4'-dinitrostilbene-2,2'-disulphonate (52% content of free dinitro-acid of molecular weight 430, which according to thin layer chromatography contains, per 100 g of solids, 0.6 g of 4,4'-dinitrodibenzyl-2,2'-disulphonic acid, 0.5 g of an unknown starting compound, 0.2 g of 4-nitrotoluene-2-sulphonic acid and 0.2 g of 4-nitrobenzaldehyde-2-sulphonic acid) are dissolved in 1,400 g of hot water. 15 g of water-moist Raney cobalt are added to the solution and the pH is adjusted to 6.6 by blowing in carbon dioxide. Hydrogenation is carried out in a 3 liter stirred autoclave made of steel, at 120°–125° C and in the pressure range of 50–80 bars of $H_2$. After 30 minutes, the absorption of hydrogen has ceased. The catalyst is separated from the cooled solution by filtration. 2,007 g of a light yellow solution of pH value 7.0, which consumes 4.84 g of nitrite per 100 g, are obtained; this corresponds to a content of 13.0% of free 4,4'-diaminostilbene-2,2'-disulphonic acid (molecular weight 370).

According to a thin layer chromatogram analysis, the solution contains, per 100 g of pure diamino-acid, 0.9 g of 4,4'-diaminodibenzyl-2,2'-sulphonic acid, 0.5 g of unknown compounds, 0.2 g of 4-aminotoluene-2-sulphonic acid and 0.5 g of 4-aminobenzaldehyde-2-sulphonic acid.

Comparison examples

1a. The experiment of Example 1 is repeated but instead of the cobalt catalyst, 15 g of a commercially available nickel hydrogenation catalyst (approx. 45% of Ni on kieselguhr) are employed. The hydrogenation starts at 70° C and is complete after 4½ hours.

A strongly yellow-coloured salt is obtained which according to the NMR spectrum already contains, in addition to 68.5% of diamino-acid, 31.5% of the corresponding diaminodiphenylethane-disulphonic acid.

1b. If Example 1 is repeated with 6 g of Pd on charcoal (5 per cent strength), a red-coloured solution is obtained after 6 hours at 40° C and 15 bars of $H_2$, which in addition to unreduced nitro coupounds already contains 30% of the disulphonic acid salt of the diaminodiphenylethane compound.

1c. If Example 1 is repeated with 15 g of Raney nickel as the catalyst at pH 8, the amount of hydrogen required to reduce the nitro group has not yet been taken up after 10 hours at 80°–110° C and 50 bars. Diamino-acid is obtained alongside large proportions of a red product which is no longer soluble. The content of 4,4'-diaminodibenzyl-2,2'-disulphonic acid-(2,2') is about 30%.

1d. If Example (1c) is repeated at 60°–80° C and pH 7, the diaminostilbenedisulphonic acid is obtained in a strongly red-coloured form, alongside large proportions of compounds still containing nitro groups. According to the NMR spectrum, the acid already contains large proportions of a compound containing $-CH_2-CH_2-$ groups.

EXAMPLE 2

100 g of disodium 4,4'-dinitrostilbene-2,2'-disulphonate (81.6% content of free disulphonic acid of molecular weight 430, with the following impurities per 100 g of free disulphonic acid of molecular weight 430: 0.5 g of 4,4'-dinitrodibenzyl-2,2'-disulphonic acid, 0.5 g of 4-nitrotoluene-2-sulphonic acid, 0.2 g of 4-nitrobenzaldehyde-2-sulphonic acid and 1.0 g of various unknown compounds) are dissolved in 400 ml of hot water and 10 g of a commercial cobalt-on-kieselguhr catalyst (35% Co, reduced in a stream of $H_2$ at 250° C) are added. $CO_2$ is passed in until a pH value of 6.5 has been obtained. The solution together with the catalyst is heated in an autoclave with stirrer under 40 bars of $H_2$ to 120°–125° C. As soon as this temperature range has been reached, the absorption of hydrogen commences. When the pressure has dropped to 40 bars, it is made up to 60 bars of $H_2$. After 50 minutes the absorption of $H_2$ has ended.

After cooling, releasing the pressure and filtering, 541 g of a light yellow solution which consumes 4.7 g of nitrite per 100 g are obtained; this corresponds to a content of 12.6% of diaminostilbenedisulphonic acid of molecular weight 370 (97% of theory).

Examination by thin layer chromatography showed the following impurities per 100 g of diaminostilbenedisulphonic acid of molecular weight 370: 0.5 g of 4,4'-diaminodibenzyl-2,2'-disulphonic acid, 0.5 g of 4-aminotoluene-2-sulphonic acid, 0.3 g of 4-aminobenzaldehyde-2-sulphonic acid and 1.2 g of various unknown compounds.

We claim:

1. Process for the preparation of 4,4'-diaminostilbene-2,2'-disulphonic acid or its alkali metal salt by catalytic hydrogenation of an alkali metal salt of 4,4'-dinitrostilbene-2,2'-disulphonic acid in an aqueous medium, characterized in that the hydrogenation is carried out with a catalyst consisting essentially of cobalt at 70°–180° C, 5–150 bars of hydrogen, and a pH of 6.0–8.5.

2. Process according to claim 1, characterized in that the hydrogenation is carried out at a temperature of 100°–160° C and 20–120 bars of $H_2$.

3. Process according to claim 1, characterized in that the hydrogenation is carried out at a temperature of 120°–125° C and 20–120 bars.

4. Process according to claim 1, characterized in that Raney cobalt is used as the catalyst.

5. Process according to claim 1, characterized in that cobalt precipitated on a support is used as the catalyst.

6. Process according to claim 1, characterized in that the hydrogenation is carried out at a pH value between 6.2 and 7.0.

* * * * *